US011566294B2

(12) United States Patent
Kirveskari et al.

(10) Patent No.: US 11,566,294 B2
(45) Date of Patent: Jan. 31, 2023

(54) METHOD FOR DETECTING THE PRESENCE OF A HYPERVIRULENT *CLOSTRIDIUM DIFFICILE* STRAIN

(71) Applicant: Mobidiag Ltd, Espoo (FI)

(72) Inventors: Juha Kirveskari, Espoo (FI); Jaakko Kurkela, Espoo (FI)

(73) Assignee: Mobidiag Ltd., Espoo (FI)

( * ) Notice: Subject to any disclaimer, the term of this patent is extended or adjusted under 35 U.S.C. 154(b) by 1234 days.

(21) Appl. No.: 15/532,132

(22) PCT Filed: Dec. 18, 2015

(86) PCT No.: PCT/FI2015/050911
§ 371 (c)(1),
(2) Date: Jun. 1, 2017

(87) PCT Pub. No.: WO2016/097491
PCT Pub. Date: Jun. 23, 2016

(65) Prior Publication Data
US 2019/0345540 A1   Nov. 14, 2019

(30) Foreign Application Priority Data
Dec. 19, 2014 (FI) .................................... 20146124

(51) Int. Cl.
*C12Q 1/68* (2018.01)
*C12Q 1/689* (2018.01)

(52) U.S. Cl.
CPC ....... *C12Q 1/689* (2013.01); *C12Q 2600/158* (2013.01); *C12Q 2600/16* (2013.01)

(58) Field of Classification Search
CPC ............. C12Q 1/689; C12Q 2600/158; C12Q 2600/16; C12Q 1/6851
See application file for complete search history.

(56) References Cited

U.S. PATENT DOCUMENTS

2013/0302813 A1   11/2013   Davis et al.

FOREIGN PATENT DOCUMENTS

| CN | 103361434 A | 10/2013 | |
| EP | 2419527 B1 | 6/2013 | |
| EP | 2671953 A1 | 12/2013 | |
| WO | WO9845706 A1 | 10/1998 | |
| WO | WO2010062897 A1 | 6/2010 | |
| WO | WO2010116290 A1 | 10/2010 | |
| WO | WO201287135 A1 | 6/2012 | |
| WO | WO-2012087135 A1 * | 6/2012 | ............. C12Q 1/689 |

OTHER PUBLICATIONS

Farrow. Analysis of Clostridial MLS Resistance Determinants (Thesis). 2002. Monash University. (Year: 2002).*
He et al. (PNAS, 2010, 107(16)7527-7532) (Year: 2010).*
Lowe et al. (Nucleic Acids Research, 1990, 18(7):1757-1761) (Year: 1990).*
Farrow et al. (Microbiology, 2001, 147, p. 2717-2728) (Year: 2001).*
Murray et al. (BMC Infect Dis, 2009, 9(103), p. 1-11) (Year: 2009).*
Silja Mentula, Sanna Laakso, Outi Lyytikäinen & Juha Kirveskari (2015) Differentiating virulent 027 and non-027 Clostridium difficile strains by molecular methods, Expert Review of Molecular Diagnostics, 15:9, 1225-1229 (Year: 2015).*
Ramos et al. (Microbiol and Molec Biol Reviews, 2005, 69(2):326-356) (Year: 2005).*
Genbank accession #AF109075 2006, Clostridium difficile Ilvd (ilvd) gene, partial cds; HydR (hydR), HydD (hydD), erm leader peptide, rRNA methyltransferase Erm1B, EffR (effR), EffD (effD), IspD (ispD), and FlxD (flxD) genes, complete cds; transposon Tn5398, complete sequence; and unknown genes. (Year: 2006).*
Eastwood et al., J of Clin Microbiol, 2009, 47(10):3211-3217 (Year: 2009).*
Database Genbank: Clostridium diffcile R20291 complete genome. Nucleotides 2109065-2109183 NCBI [retrieved May 25, 2015]. Accession No. FN545816.1. 21.4.2010.
Database Genbank: Clostridium difficile ilvd (ilvd) gene, partial cds; HydR (hydR), HydD (hydD), erm leader peptide, rRNA methyltransferase Erm1B (erm1B), rRNA methyltransferase Erm2B (erm2B), EffR (effR), EffD (effD), IspD (ispD), and FlxD (flxD) genes, complete cds; transposon Tn5398, complete, AF109075 Dec. 22, 2006 retrieved May 25, 2015.
Denève et al: New trends in Clostridium difficile virulence and pathogenesis Intl Jnl of Antimicrobial Agents, 2009, vol. 33, pp. 24-28.
Eastwood et al: Comparison of Nine Commercially Available Clostridium difficile Toxin Detection Assays, a Real-Time PCR Assay for C. difficile tcdB. and a Glutamate Dehydrogenase Detection Assay to Cytotoxin Testing and Cytotoxigenic Culture Methods. Jnl of Clinical Microbiology, Oct. 2009, vol. 47, No. 10, pp. 3211-3217.
Farrow et al: Genomic analysis of the erythromycin resistance element Tn5398 from Clostridium difficile. Micorbiology, 2001, vol. 147, pp. 2717-2728.
Forgetta et al: Fourteen-genome comparison identifies DNA markers for severe-disease-associated strains of Clostridium difficile. Journal of Clinical Microbiology, Jun. 2011, vol. 49, No. 6, pp. 2230-2238.
Hirvonen et al: Evaluation of a New Automated Homogeneous PCR Assay, GenomEra C. difficile, for Rapid Detection of Toxigenic Clostridium difficile in Fecal Specimens Jnl of Clinical Microbiology, Sep. 2013, vol. 51, No. 9, pp. 2908-2912.

(Continued)

*Primary Examiner* — Stephanie K Mummert
(74) *Attorney, Agent, or Firm* — Adam M. Breier; Jeffrey E. Landes

(57) ABSTRACT

The present invention provides a nucleic acid amplification based method for detecting a hypervirulent *Clostridium difficile* strain in a biological sample. The present invention is based on the use of oligonucleotide primers and probes specific to negative and positive markers in hypervirulent *Clostridium difficile* genome.

30 Claims, No Drawings
Specification includes a Sequence Listing.

(56) References Cited

OTHER PUBLICATIONS

Houser et al: Real-Time Multiplex Polymerase Chain Reaction Assay for Rapid Detection of Clostridium difficile Toxin-Encoding Strains. Foodborne Pathogens and Disease, 2010, vol. 7, No. 6, pp. 719-726.
Janvilisri et al: Development of a microarray for identification of pathogenic *Clostridium* spp. Diac Microbio. and Infectious Disease, vol. 66, pp. 140-147.
Knetsch et al: Genetic markers for Clostridium difficile lineages linked to hypervirulence. Microbiology, 2011, vol. 157, pp. 3113-3123.
Marsden et al: Array comparative hybridisation reveals a high degree of similarity between UK and European clinical isolates of hypervirulent Clostridium difficile. BMC Genomics, 2010, vol. 11, pp. 1-16.
Rupnik et al: Clostridium difficile infection: new developments in epidemiology and pathogenesis. Nature Reviews Microbiology, Jul. 2009, vol. 7, pp. 526-536.
Stabler et al: Comparative genome and phenotypic analysis of Clostridium difficile 027 strains provides insight into the evolution of a hypervirulent bacterium—Genome Biology, 2009, vol. 10, p. R102-R102.15.
Database Genbank: Crostridium difficile strain R20291 transposon Tn6103, complete sequence. Brouwer, M.S. et al., Accession No. BK008007.1, Sep. 22, 2011.
Yodosha Co Ltd: Newest methods for PCR (Separate volume of experimental medicine: Biochemistry manual set-up series) (Written in the Japanese language), pp. 18-19.

\* cited by examiner

METHOD FOR DETECTING THE PRESENCE OF A HYPERVIRULENT *CLOSTRIDIUM DIFFICILE* STRAIN

The present invention relates to the field of nucleic acid amplification based diagnostic assays. More specifically, the present invention provides a PCR based method for detecting a hypervirulent *Clostridium difficile* strain, preferably toxin producing *Clostridium difficile* strain 027, in a biological sample, such as a stool sample. The present invention is based on the use of oligonucleotide primers and probes specific to negative and positive markers for hypervirulent *Clostridium difficile* strains.

BACKGROUND OP THE INVENTION

*C. difficile* infection (CDI) is a toxin-mediated intestinal disease. The clinical outcomes of CDI can range from asymptomatic colonization to more severe disease syndromes, including severe diarrhoea, abdominal pain, fever and leukocytosis. *C. difficile* is recognized as the main cause of infectious diarrhoea that develops in patients after hospitalization and antibiotic treatment. Therefore, CDI is now considered to be one of the most important of health care-associated infections. Further, non-hospital-associated reservoirs of *C. difficile* are also emerging, and *C. difficile* is capable of spreading in animal hosts (Denéve et al., 2009; Rupnik et al. 2009).

*C. difficile* testing methods currently include cytotoxigenic culture methods, cytotoxin assays (CYT) detecting the toxins A and B produced by *C. difficile*, PCR based assays for detection of the tcdB gene of *C. difficile*, and assays for detection of *C. difficile*-specific glutamate dehydrogenase (GDH) (Eastwood et al. 2009).

In the prior art, the PCR based test have been found to be reliable, sensitive, and specific diagnostic tools for rapid screening and identification of samples containing *C. difficile* (Eastwood et al., 2009, Hirvonen et al., 2013; Houser et al., 2010 and WO2012087135). In commercial use is a method disclosed by WO2010116290 (Philips) relating to a multiplex PCR assay for the detection of a toxigenic *C. difficile* strain by analysing the presence or absence of the cytotoxin tcdB gene and deletions in the tcdC gene.

Although a number of PCR based assays for detecting toxin producing *Clostridium difficile* strain are already disclosed, there is still a need in the field for a PCR assay which is able to provide high specificity and reliability for the detection of those *C. difficile* strains which are hypervirulent. The present inventors have now located DNA sequence regions in *Clostridium difficile* genome that are surprisingly well-suited for specific and sensitive amplification of negative and positive markers relating to hypervirulent *Clostridium difficile* strains.

The sample matrix, which in diarrhoea diagnostics is commonly a stool or food sample, is likely to contain a host of PCR inhibitors. This reduces amplification efficiency of the PCR reaction and thus even more careful optimization is expected from the amplicon design step to verify that all templates and copy numbers are amplified equally but also efficiently enough. Hence, oligonucleotide design enabling high PCR efficiency (optimally as close to 100% as possible) is required. The detection method used may also affect amplification efficiency and/or bias.

The present inventors have now located DNA sequence regions that are well suited for specific and sensitive amplification and quantification of diarrhoea causing hypervirulent *Clostridium difficile* strains. The amplicons have been designed to be so specific that they can be combined into any multiplex sets with each other. Naturally a prerequisite to this is that all the disclosed amplicons have also been designed to amplify in the same reaction and cycling conditions. The aim of the invention is to replace antigen testing and culturing as a screening test for hypervirulent *Clostridium difficile*, and thus provide process improvements for the laboratory and clinical benefits in improved patient management by providing rapidly a rich set of information. Further, infection control could benefit if clinical microbiology laboratories could readily differentiate between non-toxigenic *C. difficile* and hypervirulent *C. difficile*.

SUMMARY OF THE INVENTION

One object of the present invention is to provide a method of detecting the presence of a hypervirulent *Clostridium difficile* strain in a biological sample, the method comprising: performing a nucleic acid amplification reaction comprising DNA extracted from the biological sample as a template, a first oligonucleotide primer set specific for amplifying a target sequence in the *C. difficile* hydR gene in the reaction, wherein said hydR gene comprises a sequence corresponding to SEQ ID NO:1, and a second oligonucleotide primer set specific for amplifying at least part of the target sequence corresponding to *C. difficile* sequence set forth in SEQ ID NO:2 in the reaction.

Another object of the present invention is to provide an oligonucleotide primer set comprising an oligonucleotide comprising or consisting of at least 10 contiguous nucleotides present in a nucleotide sequence as set forth in SEQ ID NO:3 and an oligonucleotide comprising or consisting of at least 10 contiguous nucleotides present in a nucleotide sequence as set forth in SEQ ID NO: 4, wherein the oligonucleotide primer set amplifies a target sequence in the *C. difficile* hydR gene.

Another object of the present invention is to provide an oligonucleotide primer set comprising an oligonucleotide comprising or consisting of at least 10 contiguous nucleotides present in a nucleotide sequence as set forth in SEQ ID NO: 5 and an oligonucleotide comprising or consisting of at least 10 contiguous nucleotides present in a nucleotide sequence as set forth in SEQ ID NO: 6, wherein the oligonucleotide primer set amplifies a specific target sequence in *C. difficile* genome.

Another object of the present invention is to provide an oligonucleotide primer set comprising an oligonucleotide comprising or consisting of at least 10 contiguous nucleotides present in a nucleotide sequence as set forth in SEQ ID NO: 11 and an oligonucleotide comprising or consisting of at least 10 contiguous nucleotides present in a nucleotide sequence as set forth in SEQ ID NO: 12, wherein the oligonucleotide primer set amplifies a target sequence in the *C. difficile* tcdB gene.

Another object of the present invention is to provide a kit for detecting a hypervirulent *Clostridium difficile* strain in a biological sample, the kit comprising: an oligonucleotide primer set as defined above; and a reagent for performing amplification of a nucleic acid in a nucleic acid amplification reaction.

DETAILED DESCRIPTION OF THE INVENTION

The purpose of the method of the present invention is to serve as a primary microbiological screening test for the qualitative identification of hypervirulent *C. difficile*, and a recurrent disease associated ribotype 027. The method is preferably performed from DNA extracted directly from a biological sample, such as a stool sample, without the use of an enrichment culture. Preferably, the method of the invention is a PCR-based *C. difficile* assay: such as a qPCR assay, or a qualitative multiplexed nucleic acid-based in vitro diagnostic test intended for detecting of nucleic acid markers corresponding to the detection and identification of hypervirulent *Clostridium difficile* and toxin producing 027 ribotype selective markers.

As used herein, a "target sequence" present in a nucleic acid sample is a strand of *C. difficile* DNA to be primed and extended by a "primer". A target sequence may be either single-stranded or in a duplex with its complementary sequence. Target sequence as defined in the present invention is preferably purified to some degree prior to the amplification reactions described herein.

As used herein, the term "oligonucleotide" refers to any polymer of two or more of nucleotides, nucleosides, nucleobases or related compounds used as a reagent in the DNA amplification methods, such as primers and probes. The oligonucleotide may be DNA and/or RNA and/or analogs thereof. The term oligonucleotide does not denote any particular function to the reagent; rather, it is used generically to cover all such reagents described herein. Specific oligonucleotides of the present invention are described in more detail below. As used herein, an oligonucleotide can be virtually any length, limited only by its specific function in the DNA amplification reaction. Oligonucleotides of a defined sequence and chemical structure may be produced by techniques known to those of ordinary skill in the art, such as by chemical or biochemical synthesis, and by in vitro or in vivo expression from recombinant nucleic acid molecules, e.g., bacterial or viral vectors. Oligonucleotides may be modified in any way, as long as a given modification is compatible with the desired function of a given oligonucleotide. One of ordinary skill in the art can easily determine whether a given modification is suitable or desired for any given oligonucleotide of the present invention. Modifications include, but are not limited to base modifications, sugar modifications or backbone modifications. While design and sequence of oligonucleotides for the present invention depend on their function as described below, several variables must generally be taken into account. Among the most critical are: length, G/C content, melting temperature (Tm), Gibb free energy (G), specificity, self-complementarity and complementarity with other oligonucleotides in the system, polypyrimidine (T, C) or polypurine (A, G) stretches, and the 3'-end sequence. Controlling for these and other variables is a standard and well-known aspect of oligonucleotide design, and various computer programs are readily available to screen large numbers of potential oligonucleotides for optimal ones.

As used herein, the term "PCR reaction", "PCR amplifying" or "PCR amplification" refers generally to cycling polymerase-mediated exponential amplification of nucleic acids employing primers that hybridize to complementary strands, as described for example in Innis et al, PCR Protocols: A Guide to Methods and Applications, Academic Press (1990). Devices have been developed that can perform thermal cycling reactions with compositions containing fluorescent indicators which are able to emit a light beam of a specified wavelength, read the intensity of the fluorescent dye, and display the intensity of fluorescence after each cycle. The amplification product contains a sequence having sequence identity with a target nucleic acid sequence or its complement and can be detected with, for example, an intercalating dye or a detection probe having specificity for a region of the target nucleic acid sequence or its complement. The PCR reaction as defined in the present invention is preferably performed as a real-time PCR assay.

As used herein, the term "probe" refers to any of a variety of signalling molecules indicative of amplification. For example, SYBR® Green and other DNA-binding dyes are detector probes. Some detector probes can be sequence-based, for example 5' nuclease probes. Various detector probes are known in the art, for example TaqMan® probes (See U.S. Pat. No. 5,538,848). The melting temperature, Tm, of the probes can be increased by addition of modified nucleotides. The amount of modified nucleotides in one probe is preferably 1, 3, 4 or more. The modified nucleotide can be a LNA nucleotide (Exiqon A/S), minor groove binder (MGB™), SuperBase, or Peptide Nucleic Acid (PNA) or any other modification increasing the Tm of the probe.

A person skilled in the art knows that amplified target sequences, i.e. amplicons, naturally vary in related strains. This minor variation can be taken into account while designing primers suitable to amplify said amplicons in the method of the present invention.

Preferably, at least 50, 60, 70, 80, 90 or 100 nucleotides long sequence of each of the target amplicons selected from the group consisting of SEQ ID NOS:1, 2 and 10 is amplified in the method.

Preferably, the primers and probes comprise the sequences as defined in the claims and are less than 30, 35, 40, 45, 50 or 55 nucleotides long, and more preferably, less than 50 nucleotides long. Each of the present primers and probes can also be defined as consisting of at least 10, 15, 16, 17, 18, 19 or 20 contiguous nucleotides present in any one of primer or probe sequences selected from the group consisting of SEQ ID NOS:3-9 and 11-13 or comprising a sequence selected from the group consisting of SEQ ID NOS:3-9 and 11-13.

The present invention is directed to a method of detecting the presence of a hypervirulent *Clostridium difficile* strain in a biological sample. Preferably, the method is a real-time PCR assay. The method can be performed using a DNA chip, gel electrophoresis, a radiation measurement, a fluorescence measurement, or a phosphorescence measurement. A person skilled in the art may use the primers and probes of the invention also in other methods and platforms utilizing PCR or nucleic acid amplification. Said biological sample can be, e.g., a stool sample, an environmental sample or a food sample.

The method comprises the step of:

performing a nucleic acid amplification reaction comprising DNA extracted from the biological sample as a template, a first oligonucleotide primer set specific for amplifying a target sequence in the *C. difficile* hydR gene in the reaction, wherein said hydR gene comprises a sequence corresponding to SEQ ID NO:1, and a second oligonucleotide primer set specific for amplifying at least part of the target sequence corresponding to *C. difficile* sequence set forth in SEQ ID NO:2 in the reaction. Preferably, the method comprises a step of detecting the presence of a hypervirulent *Clostridium difficile* strain in said biological sample by any method capable of detecting amplified target sequences in the reaction.

The hypervirulent *Clostridium difficile* strain is detected in the sample, when the first oligonucleotide primer set does not amplify a specific product, i.e. the target sequence in hydR gene is a negative marker for hypervirulent *Clostridium difficile* strain, and the second oligonucleotide primer set amplifies a specific product, i.e. the sequence targeted by the second primer set in *C. difficile* genome is a positive marker for hypervirulent *Clostridium difficile* strains.

The most important hypervirulent *Clostridium difficile* strain detected by the present method is toxin producing *Clostridium difficile* strain 027. Thus, the present method is particularly directed to the detection of this *Clostridium difficile* strain. The presence of *C. difficile* hydR gene DNA in said sample, however, indicates that *Clostridium difficile* strain 027 is not present in the examined sample or that in addition to the presence of a toxin producing *Clostridium difficile* strain 027 there is also presence of another *Clostridium difficile* strain in the sample. A skilled person of the art is, however, aware that some of hypervirulent *C. difficile* strains are not classified as 027-ribotype strains, therefore, the present invention is also directed to the detection of hypervirulent 027-ribotype-resembling *Clostridium difficile* strains.

Preferably, the first oligonucleotide primer set targets the *C. difficile* hydR gene and amplifies the hydR sequence set forth in SEQ ID NO:1 so that at least part of the sequence is specifically amplified in the amplification reaction. More preferably, the first oligonucleotide primer set comprises an oligonucleotide comprising or consisting of at least 10 contiguous nucleotides present in the nucleotide sequence as set forth in SEQ ID NO: 3 and an oligonucleotide comprising or consisting of at least 10 contiguous nucleotides present in the nucleotide sequence as set forth in SEQ ID NO: 4, said primers amplifying at least part of the hydR sequence set forth in SEQ ID NO:1. Most preferably, the first oligonucleotide primer set comprises an oligonucleotide comprising or consisting of the nucleotide sequence as set forth in SEQ ID NO: 3 and an oligonucleotide comprising or consisting of the nucleotide sequence as set forth in SEQ ID NO: 4.

The presence of the target sequence amplified with the first oligonucleotide primer set can be detected by the use of a probe comprising or consisting of at least 10 contiguous nucleotides present in the nucleotide sequence as set forth in SEQ ID NO:7, or preferably, by the use of a probe comprising or consisting of the nucleotide sequence as set forth in SEQ ID NO:7.

The target sequence of the second oligonucleotide primer set in *C. difficile* genome corresponds to a gene encoding a putative conjugative transposon DNA recombination protein. Preferably, said second oligonucleotide primer set comprises an oligonucleotide comprising or consisting of at least 10 contiguous nucleotides present in a nucleotide sequence as set forth in SEQ ID NO: 5 and an oligonucleotide comprising or consisting of at least 10 contiguous nucleotides present in a nucleotide sequence as set forth in SEQ ID NO: 6. More preferably, the second oligonucleotide primer set comprises an oligonucleotide comprising or consisting of the nucleotide sequence as set forth in SEQ ID NO: 5 and an oligonucleotide comprising or consisting of the nucleotide sequence as set forth in SEQ ID NO: 6.

The probes for the second oligonucleotide primer set as defined in SEQ ID NO: 8 and 9 can be used as competitive probes in a same reaction to detect a G/A polymorphism in *C. difficile* genome in a position corresponding to position 12 in SEQ ID NO:8 or 9. The presence of the target sequence amplified with the second oligonucleotide primer set can be detected by the use of a probe comprising or consisting of at least 10 contiguous nucleotides present in the nucleotide sequence as set forth in SEQ ID NO:7 so that said G/A polymorphism is detected. Preferably, the target sequence amplified with the second oligonucleotide primer set is detected by the use of a probe comprising or consisting of the nucleotide sequence as set forth in SEQ ID NO:8 or 9.

The amplification reaction as defined in the method may further comprise a third oligonucleotide primer set specific for amplifying *C. difficile* toxin B gene (tcdB). The third oligonucleotide primer set amplifies at least part of nucleotide region as set forth in SEQ ID NO: 10.

Preferably, the third oligonucleotide primer set comprises an oligonucleotide comprising or consisting of at least 10 contiguous nucleotides present in the nucleotide sequence as set forth in SEQ ID NO: 11 and an oligonucleotide comprising or consisting of at least 10 contiguous nucleotides present in the nucleotide sequence as set forth in SEQ ID NO: 12.

More preferably, the third oligonucleotide primer set comprises an oligonucleotide comprising or consisting of the nucleotide sequence as set forth in SEQ ID NO: 11 and an oligonucleotide comprising or consisting of the nucleotide sequence as set forth in SEQ ID NO: 12.

The presence of the target sequence amplified with the third oligonucleotide primer set is detected by the use of a probe comprising or consisting of at least 10 contiguous nucleotides present in the nucleotide sequence as set forth in SEQ ID NO:13, preferably, by the use of a primer comprising or consisting of the nucleotide sequence as set forth in SEQ ID NO:13.

The present invention is also directed to oligonucleotide primer sets, i.e. oligonucleotides, comprising primers as defined above for the first, second or third oligonucleotide primer set or a mix thereof. The primer sets may also comprise probes as defined above for use with each of the primer sets. The present invention is also directed to the use of these oligonucleotide primer sets for the detection of the presence of a hypervirulent *Clostridium difficile* strain in a biological sample, such as a stool sample or a food sample.

The present invention also provides kits for detecting a hypervirulent *Clostridium difficile* strain in a biological sample, a kit may comprise the oligonucleotide primer set as defined above; and a reagent for performing amplification of a nucleic acid. Preferably, the reagent is selected from the group consisting of: DNA polymerase, dNTPs, and a buffer.

Another embodiment of the invention is a method of detecting the presence of a hypervirulent *Clostridium difficile* strain in a biological sample using oligonucleotide primers and probes with modified nucleotides. Generally, the use of modified nucleotides renders possible shortening of an oligonucleotide primer or probe without compromising its specificity. The amount of modified nucleotides in one primer or probe is preferably 1, 2, 3, 4 or more. The modified nucleotide can be a LNA nucleotide (Exiqon A/S), minor groove binder (MGB™), SuperBase, or Peptide Nucleic Acid (PNA) or any other nucleotide modification having the same effect on the oligonucleotide. The method comprises essentially same steps as the method described above and in the claims but is performed with at least one modified primer or probe. One example of the primers and probes for such method is:

Primer pair 1 (for the detection of hydR gene): SEQ ID NO: 3 and SEQ ID NO: 4 with probe having the sequence SEQ ID NO: 7.

Primer pair 2 (for the detection of putative conjugative transposon, pct): SEQ ID NO: 5 and SEQ ID NO: 6 with a probe having the sequence CTG T<u>A</u>G A<u>T</u>T T<u>C</u>G GT<u>A</u> CGA (SEQ ID NO: 14), wherein underlined nucleotides are modified nucleotides such as LNA.

Primer pair 3 (for the detection of tcdB gene): SEQ ID NO: 11 and SEQ ID NO: 12 with a probe having the sequence SEQ ID NO: 13.

Accordingly, a person skilled in the art would understand that the length of any of the above primers or probes may be shortened in a similar way by using at least one modified nucleotide.

The publications and other materials used herein to illuminate the background of the invention, and in particular, to provide additional details with respect to its practice, are incorporated herein by reference. The present invention is further described in the following example, which is not intended to limit the scope of the invention.

EXPERIMENTAL SECTION

Example 1

In this example, the assay of the disclosed invention was used to detect both toxin-producing and non-toxin-producing *C. difficile* strains. A total of 48 characterized samples representing 37 different ribotypes were tested. This test excluded 027 or genetically very closely related ribotypes.

The assay contains one multiplex PCR reaction which amplifies the target panel (Table 1). Identification of toxin producing *C. difficile* and differentiation of hypervirulent *C. difficile* is based on combined detection of these markers. Toxin marker: tcdB gene encodes Toxin B, 027-negative marker: hydR encodes TetR family transcriptional regulator protein and 027-positive marker: pct encodes putative conjugative transposon DNA recombination protein. Primers and probes were as defined in Table 9.

The *C. difficile* assay should give positive results from different toxin-producing *C. difficile* strains, and negative results for non-toxin-producing *C. difficile* strains. Inclusivity (analytical reactivity) is tested to account for potential genetic variation among the targets included in the panel. This example describes the results of the inclusivity of the *C. difficile* qPCR assay using well characterized strains.

TABLE 1

*C. difficile* assay target panel

| Marker | Target gene region | Description |
| --- | --- | --- |
| Toxin B | tcdB | Detects cytotoxin (Toxin B) producing *C. difficile* |
| Positive hypervirulent marker | pct | Positive hypervirulent marker is detected only from hypervirulent strains (ribotype 027) |
| Negative hypervirulent marker | hydR | Negative marker is not detected from ribotype 027 strains, but is positive for other *C. difficile* strains |

Materials and Methods 1.1 The List of the Bacterial Targets

The *C. difficile* assay covers pathogens causing gastrointestinal infections. A total of 48 characterized samples representing 37 different ribotypes were tested in this inclusivity study covering non-toxinogenic *C. difficile* and Toxin B producing *C. difficile*. The list of strains is described in Table 2. This test excluded 027 or genetically very closely related ribotypes.

Strains were collected from commercial available biobanks (ATCC, DSMZ, and Microbiologics). DNA samples were tested in concentrations less than 100 ng/µl.

TABLE 2

Amplidiag *C. difficile* GE assays inclusivity test panel

| # | Original code |
| --- | --- |
| 1 | ATCC 51695 |
| 2 | ATCC 43599 |
| 3 | ATCC 17857 |
| 4 | ATCC BAA-1871 |
| 5 | 0329P (ATCC 9689) |
| 6 | ATCC BAA-1813 |
| 7 | ATCC BAA-1874 |
| 8 | ATCC BAA-1809 |
| 9 | ATCC BAA-1810 |
| 10 | ATCC BAA-1801 |
| 11 | ATCC BAA-1382 |
| 12 | ATCC 43596 |
| 13 | ATCC 43600 |
| 14 | AHS 56050 |
| 15 | ATCC 43598 |
| 16 | 106222 |
| 17 | ATCC BAA-1808 |
| 18 | 106216 |
| 19 | ATCC BAA-1812 |
| 20 | ATCC 43601 |
| 21 | AKC 43602 |
| 22 | 0527P (ATCC 700057) |
| 23 | 106210 |
| 24 | ATCC BAA-1873 |
| 25 | ATCC BAA-1804 |
| 26 | ATCC BAA-1811 |
| 27 | AHS 55375 |
| 28 | 0833P (ATCC 43593) |
| 29 | RHC 7722 |
| 30 | AHS 26782 |
| 31 | AHS 55985 |
| 32 | ATCC BAA-1875 |
| 33 | 106090 |
| 34 | ATCC 43603 |
| 35 | ATCC 43255 |
| 36 | AHS 56035 |
| 37 | ATCC BAA-2156 |
| 38 | RHC 7727 |
| 39 | AHS 55868 |
| 40 | 106194 |
| 41 | RHC 7758 |
| 42 | ATCC BAA-1807 |
| 43 | ATCC BAA-1872 |
| 44 | ATCC BAA-1806 |
| 45 | ATCC BAA-2155 |
| 46 | ATCC BAA-1814 |
| 47 | 106073 |
| 48 | AHS 56010 |

1.2 Reagents and Instruments gPCR Reagents:
  qPCR Mastermix, Mobidiag
  Assay mixture consisting of *C. difficile* qPCR primers and probes
Devices:
  Stratagene MxPro 3000
PCR Setup
  In reaction:

| | |
| --- | --- |
| 10 µl | 2 x Mastermix |
| 5 µl | 4 x Primer mix |
| 5 µl | sample/pos. control DNA mix/DNA extraction control/H2O |
| 20 µl | TOTAL |

PCR program:

| 95° C. | 10 min | |
| 95° C. | 15 s | 45x |
| 60° C. | 60 s | |

Results

Conclusions

All 39 toxin-producing strains were identified correctly as ToxB+. All 9 non-toxin-producing strains were correctly identified as negative. No strain gave false positive identification of the 027 ribotype (toxB+, pct+, hydR+).

Controls were detected as expected, which confirmed the reliability of the results.

TABLE 3

Identification of markers toxB, pct and hydR in *C. difficile* strains.

| # | Original code | Ribotype | Characterization | toxB | pct | hydR | Result |
|---|---|---|---|---|---|---|---|
| 1 | ATCC 51695 | 001 | A+B+, Binary toxin cdtB− | + | − | + | ToxB+ |
| 2 | ATCC 43599 | 001 | A+B+, Binary toxin cdtB− | + | − | + | ToxB+ |
| 3 | ATCC 17857 | 001 | A+B+, Binary toxin cdtB− | + | − | + | ToxB+ |
| 4 | ATCC BAA-1871 | 001 | A+B+, Binary toxin cdtB− | + | − | + | ToxB+ |
| 5 | 0329P (ATCC 9689) | 001 | A+B+, Binary toxin cdtB− | + | − | + | ToxB+ |
| 6 | ATCC BAA-1813 | 002 | A+B+, Binary toxin cdtB− | + | − | + | ToxB+ |
| 7 | ATCC BAA-1874 | 002 | A+B+, Binary toxin cdtB− | + | − | + | ToxB+ |
| 8 | ATCC BAA-1809 | 009 | A−B−, Binary toxin cdtB− | − | − | + | Negative |
| 9 | ATCC BAA-1810 | 009 | A−B−, Binary toxin cdtB− | − | − | + | Negative |
| 10 | ATCC BAA-1801 | 010 | A−B−, Binary toxin cdtB− | − | − | + | Negative |
| 11 | ATCC BAA-1382 | 012 | A+B+, Binary toxin cdtB− | + | − | + | ToxB+ |
| 12 | ATCC 43596 | 012 | A+B+, Binary toxin cdtB− | + | − | + | ToxB+ |
| 13 | ATCC 43600 | 014 | A+B+, Binary toxin cdtB− | + | − | + | ToxB+ |
| 14 | AHS 56050 | 015 | A+B+, Binary toxin−, tcdC 18 bp del | + | + | + | ToxB+ |
| 15 | ATCC 43598 | 017 | A−B+, Binary toxin cdtB− | + | − | + | ToxB+ |
| 16 | 106222 | 019 | A+B+, Binary toxin+, tcdC 18 bp del | + | − | + | ToxB+ |
| 17 | ATCC BAA-1808 | 020 | A+B+, Binary toxin cdtB− | + | − | + | ToxB+ |
| 18 | 106216 | 023 | A+B+, Binary toxin+ | + | − | + | ToxB+ |
| 19 | ATCC BAA-1812 | 024 | A+B+, Binary toxin cdtB− | + | − | + | ToxB+ |
| 20 | ATCC 43601 | 031 | A−B−, Binary toxin cdtB− | − | − | + | Negative |
| 21 | ATCC 43602 | 031 | A−B−, Binary toxin cdtB− | − | − | + | Negative |
| 22 | 0527P (ATCC 700057) | 038 | A−B−, Binary toxin cdtB− | − | − | + | Negative |
| 23 | 106210 | 045 | A+B+, Binary toxin+ | + | − | + | ToxB+ |
| 24 | ATCC BAA-1873 | 053 | A+B+, Binary toxin cdtB− | + | − | + | ToxB+ |
| 25 | ATCC BAA-1804 | 053 | A+B+, Binary toxin cdtB− | + | − | + | ToxB+ |
| 26 | ATCC BAA-1811 | 057 | A+B+, Binary toxin cdtB− | + | − | + | ToxB+ |
| 27 | AHS 55375 | 058 | A+B+, Binary toxin+ | + | − | + | ToxB+ |
| 28 | 0833P (ATCC 43593) | 060 | A−B−, Binary toxin cdtB− | − | − | + | Negative |
| 29 | RHC7722 | 063 | A+B+, Binary toxin+, tcdC 18 bp del | + | − | + | ToxB+ |
| 30 | AHS 26782 | unk. 67 | A+B+, Binary toxin+, tcdC 18 bp del | + | − | + | ToxB+ |
| 31 | AHS 55985 | 075 | A+B+, Binary toxin+, tcdC 18 bp del | + | − | − | ToxB+ |
| 32 | ATCC BAA-1875 | 078 | A+B+, Binary toxin cdtB+ | + | − | + | ToxB+ |
| 33 | 106090 | 080 | A+B+, Binary toxin+, tcdC 18 bp del | + | − | − | ToxB+ |
| 34 | ATCC 43603 | 085 | A−B−, Binary toxin cdtB− | − | − | + | Negative |
| 35 | ATCC 43255 | 087 | A+B+, Binary toxin cdtB− | + | − | + | ToxB+ |
| 36 | AHS 56035 | 111 | A+B+, Binary toxin+ | + | − | + | ToxB+ |
| 37 | ATCC BAA-2156 | 118 | A+B+, Binary toxin cdtB− | + | − | + | ToxB+ |
| 38 | RHC 7727 | 122 | A+B+, Binary toxin+, tcdC 18 bp del | + | − | + | ToxB+ |
| 39 | AHS 55868 | unk. 122 | A+B+, Binary toxin+ | + | − | + | ToxB+ |
| 40 | 106194 | 126 | A+B+, Binary toxin+ | + | − | + | ToxB+ |
| 41 | RHC 7758 | 131 | A+B+, Binary toxin+, tcdC 18 bp del | + | − | + | ToxB+ |
| 42 | ATCC BAA-1807 | 140 | A−B−, Binary toxin cdtB− | − | + | + | Negative |
| 43 | ATCC BAA-1872 | 207 | A+B+, Binary toxin cdtB− | + | − | + | ToxB+ |
| 44 | ATCC BAA-1806 | 220 | A+B+, Binary toxin cdtB− | + | − | + | ToxB+ |
| 45 | ATCC BAA-2155 | 251 | A+B+, Binary toxin cdtB+ | + | − | + | ToxB+ |
| 46 | ATCC BAA-1814 | 251 | A+B+, Binary toxin cdtB+ | + | − | + | ToxB+ |
| 47 | 106073 | 254 | A+B+, Binary toxin+ | + | − | + | ToxB+ |
| 48 | AHS 56010 | 308 | A+B+, Binary toxin−, tcdC 18 bp del | + | − | + | ToxB+ |

Functionality of Controls

Positive controls were detected as positive

Negative control was detected as negative

Internal Amplification Control was detected in all samples

Example 2

In this example, the functionality of the disclosed invention to differentiate 027 ribotype detection was tested. Two very closely related ribotypes, namely 016 and 176, were included in the samples.

Materials and Methods

DATA Extraction

The DNA from *C. difficile* isolates were extracted as described below:

A colony from bacterial cultures was suspended to the 1×PBS buffer in the final concentration ca. $1.5 \times 10^8$ CFU/ml (ref. McFarlan standard 0.5). 100 µl of bacterial suspension was transferred to the off-board lysis step following the automated extraction with NucliSENS EasyMAG (bio-Mérieux) device according to the manufacturer's protocol for Generic 2.0.1 program. DNAs were eluted to the 100 µl of elution buffer. Extraction series contained Extraction Control i.e. *C. difficile* (non-toxin producing strain).

Real-time PCR and Analysis

The PCR reactions were conducted as defined in Example 1. Internal amplification control, Positive PCR control and Negative PCR control is included to the test series.

A total of 18 different 027 ribotype strains, one 016 ribotype strain and one 176 ribotype strain were tested.

TABLE 4

Identification of markers toxB, pct and hydR in *C. difficile* 027 strains.

| # | Original code | Ribotype | Characterization | toxB | pct | hydR | Result |
|---|---|---|---|---|---|---|---|
| 1 | ATCC BAA-1805 | 027 | A+B+, Binary toxin cdtB+ | + | + | − | 027+ |
| 2 | ATCC BAA-1803 | 027 | A+B+, Binary toxin cdtB+ | + | + | − | 027+ |
| 3 | 01048P (ATCC BAA-1870) | 027 | A+B+, Binary toxin cdtB+ | + | + | − | 027+ |
| 4 | CD14-038 | 027 | n/a | + | + | − | 027+ |
| 5 | CD13-177 | 027 | n/a | + | + | − | 027+ |
| 6 | CD13-032 | 027 | n/a | + | + | − | 027+ |
| 7 | CD13-221 | 027 | n/a | + | + | − | 027+ |
| 8 | CD14-078 | 027 | n/a | + | + | − | 027+ |
| 9 | CD14-072 | 027 | n/a | + | + | − | 027+ |
| 10 | CD14-161 | 027 | n/a | + | + | − | 027+ |
| 11 | CD13-097 | 027 | n/a | + | + | − | 027+ |
| 12 | CD12-100 | 027 | n/a | + | + | − | 027+ |
| 13 | CD13-305 | 027 | n/a | + | + | − | 027+ |
| 14 | CD13-056 | 027 | n/a | + | + | − | 027+ |
| 15 | CD13-004 | 027 | n/a | + | + | − | 027+ |
| 16 | CD13-247 | 027 | n/a | + | + | − | 027+ |
| 17 | CD13-245 | 027 | n/a | + | + | − | 027+ |
| 18 | CD13-108 | 027 | n/a | + | + | − | 027+ |
| 19 | AHS 55742 | 016 | A+B+, Binary toxin+, tcdC 18bp del | + | + | − | 027+ |
| 20 | AHS 26967 | 176 | A+B+, Binary toxin+, tcdC 18bp del | + | + | − | 027+ |

The assay gave a correct positive identification identification of all the 18 different 027 strains, and gave a positive identification of 016 and 176 ribotypes. Thus, the assay detects genetically closely related 016 and 176 ribotypes in addition to 027 ribotype as 027+.

Example 3

In this example, the disclosed invention was compared to a prior art method for detecting a 027 presumptive positive *C. difficile*. The assay of the invention was compared to Xpert *C. difficile*/Epi (Cepheid) test.

The Xpert *C. difficile*/Epi test uses the detection of a deletion in tcdC gene to report a positive 027 presumptive finding.

A total of 11 different strains, representing 11 different ribotypes, were tested with both methods and the results were compared.

TABLE 5

Comparison to Xpert *C. difficile*/Epi (Cepheid) test.

| | | | | GeneXpert | | | | Identification of disclosed markers | | |
|---|---|---|---|---|---|---|---|---|---|---|
| # | Original code | Ribotype | Characterization | toxB | Binary | TcdC | Result | toxB | pct | hydR | Result |
| 1 | AHS 55742 | 016 | A+B+, Binary toxin+, tcdC 18 bp del | + | + | + | toxigenic C. diff positive, 027 presumptive positive | + | + | − | 027+ |
| 2 | 106222 | 019 | A+B+, Binary toxin+, tcdC 18 bp del | + | + | + | toxigenic C. diff positive, 027 presumptive positive | + | − | + | ToxB+ |

TABLE 5-continued

Comparison to Xpert *C. difficile*/Epi (Cepheid) test.

| # | Original code | Ribo-type | Characterization | GeneXpert toxB | GeneXpert Binary | GeneXpert TcdC | GeneXpert Result | Identification of disclosed markers toxB | Identification of disclosed markers pct | Identification of disclosed markers hydR | Identification of disclosed markers Result |
|---|---|---|---|---|---|---|---|---|---|---|---|
| 3 | AHS 26782 | unk. 67 | A+B+, Binary toxin+, tcdC 18 bp del | + | + | + | toxigenic C. diff positive, 027 presumptive positive | + | − | + | ToxB+ |
| 4 | 106090 | 080 | A+B+, Binary toxin+, tcdC 18 bp del | + | + | + | toxigenic C. diff positive, 027 presumptive positive | + | − | − | ToxB+ |
| 5 | AHS 26967 | 176 | A+B+, Binary toxin+, tcdC 18 bp del | + | + | + | toxigenic C. diff positive, 027 presumptive positive | + | + | − | 027+ |
| 6 | 106210 | 045 | A+B+, Binary toxin+ | + | + | − | toxigenic C. diff positive, 027 presumptive negative | + | − | + | ToxB+ |
| 7 | RHC 7722 | 063 | A+B+, Binary toxin+, tcdC 18 bp del | + | + | − | toxigenic C. diff positive, 027 presumptive negative | + | − | + | ToxB+ |
| 8 | AHS 55985 | 075 | A+B+, Binary toxin+, tcdC 18 bp del | + | + | − | toxigenic C. diff positive, 027 presumptive negative | + | − | − | ToxB+ |
| 9 | AHS 56035 | 111 | A+B+, Binary toxin+ | + | + | − | toxigenic C. diff positive, 027 presumptive negative | + | − | + | ToxB+ |
| 10 | RHC 7727 | 122 | A+B+, Binary toxin+, tcdC 18 bp del | + | + | − | toxigenic C. diff positive, 027 presumptive negative | + | − | + | ToxB+ |
| 11 | RHC 7758 | 131 | A+B+, Binary toxin+, tcdC 18 bp del | + | + | − | toxigenic C. diff positive, 027 presumptive negative | + | − | + | ToxB+ |

The Xpert *C. difficile*/Epi test reported 5 strains to be toxigenic *C. difficile* positive, 027 presumptive positive, while none of the tested strains were actually ribotype 027. Of these 5 strains, the method of the present invention identified only 2 strains as 027 positive, so demonstrating an improved effect in differentiating between a 027 and non-027 ribotype compared to prior art. It is notable that these two *C. difficile* strains (016 and 176) have been shown to be highly related to hypervirulent *C. difficile* strains (Knetsch et al., 2011).

The identification of the disclosed markers reported 9 strains correctly as ToxB+, but not 027+, as expected. In summary, the assay of the invention identified 9/11 strains correctly as 027−, while the Xpert *C. difficile*/Epi test reported 6/11 strains correctly with regard to the presumptive negativity of 027.

Example 4

The workflow of the present invention consists of extraction of nucleic acids from stool samples (NucliSens easyMAG), real-time PCR amplification and detection of target gene regions and analysis of results.

In this example, different toxin-producing *C. difficile* strains were tested as spiked samples in stool background. A total of 35 different strains were used. Each strain was spiked into a stool sample negative for *C. difficile*. DNA was extracted from stool samples, and gPCR reactions were prepared so that the strain was present in concentrations of either 7.5 CFU/reaction or 75 CFU/reactions as illustrated in Table 6. All samples were tested in duplicate reactions.

The results demonstrate that that the strains were correctly identified as positive in all cases.

TABLE 6

Detection of different toxin-producing *C. difficile* strains in spiked stool samples.

| Original Code | CFU/rxn | Cq values of detection of markers toxB | Cq values of detection of markers 027+ | Cq values of detection of markers 027− | Cq values of detection of markers IC | Result |
|---|---|---|---|---|---|---|
| ATCC BAA-1870 | 7.5 | 37.14 | 36.13 | n/a | 28.32 | 027+ |
| ATCC 9689 | 7.5 | 34.44 | n/a | 36.47 | 27.94 | ToxB+ |
| ATCC BAA-1382 | 7.5 | 36.37 | n/a | 37.44 | 27.77 | ToxB+ |
| ATCC 17858 | 7.5 | 35.32 | n/a | n/a | 28.55 | ToxB+ |
| ATCC 43600 | 7.5 | 37.74 | n/a | 37.21 | 28.68 | ToxB+ |
| ATCC 43596 | 7.5 | 37 | n/a | n/a | 28.29 | ToxB+ |
| ATCC 43594 | 7.5 | 37.89 | n/a | n/a | 28.31 | ToxB+ |
| ATCC 43598 | 7.5 | 36.23 | n/a | n/a | 28.7 | ToxB+ |
| ATCC BAA-1803 | 7.5 | 37.14 | 34.99 | n/a | 28.46 | 027+ |
| ATCC BAA-1808 | 7.5 | 35.7 | n/a | 34.32 | 28.37 | ToxB+ |
| ATCC BAA-1811 | 7.5 | 35.66 | n/a | 35.92 | 28.5 | ToxB+ |
| ATCC BAA-1812 | 7.5 | 37.13 | n/a | 37.67 | 28.43 | ToxB+ |
| ATCC BAA-1813 | 7.5 | 38.07 | n/a | 37.5 | 28.43 | ToxB+ |
| ATCC BAA-1815 | 7.5 | 37.6 | n/a | 36.11 | 28.28 | ToxB+ |
| ATCC BAA-1872 | 7.5 | 35.38 | n/a | 36.6 | 28.36 | ToxB+ |
| ATCC BAA-1875 | 7.5 | 36.84 | n/a | 37.56 | 28.36 | ToxB+ |
| ATCC BAA-2155 | 7.5 | 35.85 | n/a | 35.74 | 28.59 | ToxB+ |
| ATCC BAA-2156 | 7.5 | 35.73 | n/a | 35.67 | 28.3 | ToxB+ |
| ATCC BAA-1804 | 7.5 | 37.37 | n/a | 35.5 | 28.46 | ToxB+ |
| ATCC BAA-1806 | 75 | 35.7 | n/a | 35.33 | 28.97 | ToxB+ |
| CD14-038 | 75 | 36.09 | 35.08 | n/a | 29.12 | 027+ |
| CD13-177 | 75 | 34.53 | 34.21 | n/a | 29.05 | 027+ |
| CD13-032 | 75 | 34.72 | 34.6 | n/a | 29.13 | 027+ |
| CD13-221 | 75 | 36.09 | 37.14 | n/a | 29.42 | 027+ |
| CD14-078 | 75 | 32.07 | 33.3 | n/a | 29.12 | 027+ |
| CD14-072 | 75 | 32.9 | 27.53 | 43.92 | 27.52 | 027+ |
| CD14-161 | 75 | 33.53 | 35.89 | n/a | 29.24 | 027+ |
| CD13-097 | 75 | 32.72 | 33.83 | n/a | 29.14 | 027+ |
| CD12-100 | 75 | 38.56 | 36.27 | n/a | 29.34 | 027+ |
| CD13-305 | 75 | 35.97 | 39.19 | n/a | 29.43 | 027+ |
| CD13-056 | 75 | 35.46 | 35.02 | n/a | 29.14 | 027+ |
| CD13-004 | 75 | 33.22 | 34.07 | n/a | 28.93 | 027+ |
| CD13-247 | 75 | 33.75 | 34.59 | n/a | 29.08 | 027+ |
| CD13-245 | 75 | 33.08 | 34.24 | n/a | 29.02 | 027+ |
| CD13-108 | 75 | 34.55 | 36.18 | n/a | 29.04 | 027+ |

IC = internal control, controls PCR inhibition
CFU/rxn = colony forming units/reaction
Two replicates per sample

Example 5

This example describes results from a study of potential false positive results in the *C. difficile* PCR assay due to a cross-reaction. Sample material for this designed assay is stool sample. Therefore, pathogens (bacteria, viruses and parasites) associated with gastrointestinal infections, and which are not covered by assay panel, can cause potential cross-reaction. Also bacteria included to commensal flora may cross-react. Furthermore, pathogens including to the assay target panel are added to the cross-reaction study since only the target pathogen should be detected and no cross-reaction among other targets should happen.

Materials and Methods

Reagents, devices and samples
qPCR Reagents:
  Mobidiag's qPCR Mastermix (MM)
  Assay mixture consisting of *C. difficile* qPCR primers and probes (see Table 9)
Devices:
  Stratagene Mxp3000
PCR Setup In reaction:

| | |
|---|---|
| 10 µl | 2 x MM |
| 5 µl | 4 x Primer mix |
| 5 µl | sample/pos. Control DNA mix/H2O |
| 20 µl | |

Pos. Control = template mix

| | | |
|---|---|---|
| 95° C. | 10 min | |
| 95° C. | 15 s | 40x |
| 60° C. | 1 min | |

Samples:
DNA (or RNA) extracted from 127 pathogens. Strains have been mainly collected from commercial available biobanks (ATCC, DSMZ, Microbiologics Qnostics and Vircell). Some strains are added from Mobidiag biobank and those strains have been originally purified from patient samples and characterized by HUSLAB (Helsinki University central hospital laboratory).

The amount of DNA was determined by 16S rRNA assay or by NanoDrop.

TABLE 7

Cross-reaction results.

| # | Species | Result | # | Species, cont. | Result |
|---|---|---|---|---|---|
| 1 | *Acinetobacter baumannii* | Negative | 65 | *Haemophilus parainfluenzae* | Negative |
| 2 | *Actinomyces actinomycetemcomitans* | Negative | 66 | *Helicobacter mustelae* | Negative |
| 3 | *Actinomyces israelii* | Negative | 67 | *Helicobacter pylori* | Negative |
| 4 | *Actinomyces naeslundii* | Negative | 68 | *Helicobacter pylori* | Negative |
| 5 | *Aspergillus fumigatus* | Negative | 69 | Human adenovirus 40 | Negative |
| 6 | Astrovirus | Negative | 70 | Human adenovirus 41 | Negative |
| 7 | *Bacillus cereus* | Negative | 71 | Human herpesvirus 2 | Negative |
| 8 | *Bacillus subtilis* | Negative | 72 | *Kingella kingae* | Negative |
| 9 | *Bacteroides fragilis* | Negative | 73 | *Klebsiella oxytoca* | Negative |
| 10 | *Bacteroides thetaiotaomicron* | Negative | 74 | *Klebsiella pneumoniae* subsp. *pneumoniae* | Negative |
| 11 | *Bacteroides vulgatus* | Negative | 75 | *Kluyvera intermedia* | Negative |
| 12 | *Campylobacter coli* | Negative | 76 | *Lactobacillus acidophilus* | Negative |
| 13 | *Campylobacter fetus* | Negative | 77 | *Lactobacillus casei* | Negative |
| 14 | *Campylobacter jejuni* subsp. *jejuni* | Negative | 78 | *Lactococcus* sp. | Negative |
| 15 | *Campylobacter lari* | Negative | 79 | *Listeria monocytogenes* | Negative |
| 16 | *Candida albicans* | Negative | 80 | *Micrococcus luteus* | Negative |
| 17 | *Candida glabrata* | Negative | 81 | *Moraxella catarrhalis* | Negative |
| 18 | *Candida krusei* | Negative | 82 | *Morganella morganii* subsp. *morganii* | Negative |
| 19 | *Chromobacterium violaceum* | Negative | 83 | *Neisseria lactamica* | Negative |
| 20 | *Citrobacter amalonaticus* | Negative | 84 | *Neisseria sicca* | Negative |
| 21 | *Citrobacter braakii* | Negative | 85 | Norovirus genogroup 1 | Negative |
| 22 | *Citrobacter freundii* | Negative | 86 | Norovirus genogroup 2 | Negative |
| 23 | *Citrobacter koserii* | Negative | 87 | *Pasteurella multocida* | Negative |
| 24 | *Clostridium histolyticum* | Negative | 88 | *Peptostreptococcus micros* | Negative |
| 25 | *Clostridium perfringens* | Negative | 89 | *Plesiomonas shigelloides* | Negative |
| 26 | *Clostridium septicum* | Negative | 90 | *Porphyromonas gingivalis* | Negative |
| 27 | *Clostridium sordellii* | Negative | 91 | *Prevotella intermedia* | Negative |
| 28 | *Clostridium sporogenes* | Negative | 92 | *Prevotella loescheii* | Negative |
| 29 | *Clostridium tetani* | Negative | 93 | *Propionibacterium acnes* | Negative |
| 30 | *Corynebacterium amycolatum* | Negative | 94 | *Proteus mirabilis* | Negative |
| 31 | *Corynebacterium diphtheriae* | Negative | 95 | *Proteus vulgaris* | Negative |
| 32 | *Cronobacter sakazakii* | Negative | 96 | *Providencia rettgeri* | Negative |
| 33 | *Cryptosporidiumn parvum* | Negative | 97 | *Providencia stuartii* | Negative |
| 34 | Cytomegalovirus | Negative | 98 | *Pseudomonas aeruginosa* | Negative |
| 35 | *Desulfovibrio* sp. | Negative | 99 | *Raoutella ornithinolytica* | Negative |
| 36 | *Dientamoeba fragilis* | Negative | 100 | *Rhodococcus equi* | Negative |
| 37 | *Edwardsiella tarda* | Negative | 101 | Rotavirus A | Negative |
| 38 | *Eggerthella lenta* | Negative | 102 | *Saccharomyces kudriaczevii* | Negative |
| 39 | *Elizabethkingia meningoseptica* | Negative | 103 | *Salmonella bongori* | Negative |
| 40 | *Entamoeba histolytica* | Negative | 104 | *Salmonella enterica* subsp. *enterica, Typhimurium* | Negative |
| 41 | *Enterobacter aerogenes* | Negative | 105 | Sapovirus | Negative |
| 42 | *Enterobacter cloacae* | Negative | 106 | *Serratia liquefaciens* | Negative |
| 43 | *Enterobacter hormaechei* subsp. *hormaechei* | Negative | 107 | *Serratia marcescens* subsp. *marcescens* | Negative |
| 44 | *Enterococcus casseliflavus* | Negative | 108 | *Shigella boydii* | Negative |

TABLE 7-continued

Cross-reaction results.

| # | Species | Result | # | Species, cont. | Result |
|---|---|---|---|---|---|
| 45 | Enterococcus faecalis | Negative | 109 | Staphylococcus aureus | Negative |
| 46 | Enterococcus faecium | Negative | 110 | Staphylococcus epidermidis | Negative |
| 47 | Enterococcus gallinarum | Negative | 111 | Staphylococcus lugdunensis | Negative |
| 48 | Escherichia coli, non toxigenic | Negative | 112 | Stenotrophomonas maltophilia | Negative |
| 49 | Escherichia coli, EAEC | Negative | 113 | Streptococcus agalactiae | Negative |
| 50 | Escherichia coli, EHEC | Negative | 114 | Streptococcus anginosus | Negative |
| 51 | Escherichia coli, EIEC | Negative | 115 | Streptococcus bovis | Negative |
| 52 | Escherichia coli, EPEC | Negative | 116 | Streptococcus dysgalactiae subsp. equisimilis | Negative |
| 53 | Escherichia coli, ETEC | Negative | 117 | Streptococcus oralis | Negative |
| 54 | Escherichia fergusonii | Negative | 118 | Streptococcus pneumoniae | Negative |
| 55 | Escherichia hermanii | Negative | 119 | Streptococcus pyogenes | Negative |
| 56 | Escherichia vulneris | Negative | 120 | Streptococcus salivarius | Negative |
| 57 | Fusarium solani | Negative | 121 | Streptococcus viridans | Negative |
| 58 | Fusobacterium necrophorum subsp. necrophorum | Negative | 122 | Streptococcus viridans | Negative |
| 59 | Fusobacterium nucleatum subsp. nucleatum | Negative | 123 | Streptomyces spp. | Negative |
| 60 | Gardnerella vaginalis | Negative | 124 | Vibrio parhaemolyticus | Negative |
| 61 | Giardia lamblia | Negative | 125 | Vibrio vulnificus | Negative |
| 62 | Gordonia ssp. | Negative | 126 | Yersinia enterocolitica subsp. enterocolitica | Negative |
| 63 | Haemophilus ducreyi | Negative | 127 | Yersinia pseudotuberculosis | Negative |
| 64 | Haemophilus influenzae | Negative | | | |

Functionality of Controls

Positive controls were detected as positive

Negative controls were detected as negative

Results

The cross-reactivity test showed no false positives.

TABLE 9

Oligonucleotide primers and probes.

| Oligo Name | Sequence 5' → 3' | Internal modification | 5' modification | 3' modification | |
|---|---|---|---|---|---|
| F_tcdb_01 | GGAAGTGAATGTATATGAAAACC | | | | SEQ ID NO: 11 |
| R_tcdb_01 | GCCATTTTTTCTAACTGTTTTC | | | | SEQ ID NO: 12 |
| P_tcdb_01_dq | AGAAAGGAGGATATATAAAAGAGTTTTAGC | ZEN | 6-FAM | Iowa Black® FQ | SEQ ID NO: 13 |
| F_hyd_01 | CGAACTTCCTCTATTAAAGC | | | | SEQ ID NO: 3 |
| R_hyd_01 | GTGCAATGTATCATCACTTTA | | | | SEQ ID NO: 4 |
| P_hyd_01 | AATCATTCGCACTATGAACAACCAATT | | ROX | Iowa Black® RQ | SEQ ID NO: 7 |
| F_pct_01 | ACGGAAACATCAAATAACG | | | | SEQ ID NO: 5 |
| R_pct_01 | GTACCTTTACCAATGTTATATG | | | | SEQ ID NO: 6 |

TABLE 9-continued

Oligonucleotide primers and probes.

| Oligo Name | Sequence 5' → 3' | Internal modification | 5' modification | 3' modification | |
|---|---|---|---|---|---|
| P_pct_03_dq | TCTGTAGATTTCGGTACGAAAACTTCA | ZEN | HEX | Iowa Black® FQ | SEQ ID NO: 8 |
| S_pct_03 | TCTGTAGATTTTGGTACGAAAACTTCA | | | Iowa Black® FQ | SEQ ID NO: 9 |

TABLE 10

Amplicons amplified by the oligonucleotide sets.

| Name | Sequence 5' → 3' | Size bp | |
|---|---|---|---|
| C.dif_pct_hypV | ACGGAAACATCAAATAACGAATTGACAATTTCTGTAGATTTCGGTACGAAAACTTCATGGGAAAGCAGCTTGTAACCCAATTAAATGAAATACCATATATAACATTGGTAAAGGTAC | 119 | SEQ ID NO: 2 |
| C.dif_hydR_01 | CGAACTTCCTCTATTAAAGCGAATGGGATTTTTTCTAACCAGCTACAATGTACCATTTTTCTACGTGTGTAATCATTCGCACTATGAACAACCAATTCTATTATTTTTTCATTTGCTGTAAGGGTGTCATCAGCAACAAGATACTCTAAAAAATTATTCATTGTGAGTAAAGTTCTTTTGTGACACTTCTCAGTATATCTTCTTTAGTTTTAAAGTGATGATACATTGCAC | 232 | SEQ ID NO: 1 |
| C.dif_tcdB_short | GGAAGTGAATGTATATGAAAACCTAAGTAGATATTAGTATATTTTATAAATAGAAAGGAGGATATATAAAAGAGTTTTAGCATTTAGATGTAAAAATATTCAATAAAAATATTATAGTAAAGGAGAAATTTTATGAGTTTAGTTAATAGAAAACAGTTAGAAAAAATGGC | 171 | SEQ ID NO: 10 |

REFERENCES

Denéve, C., Janoira, C., Poilaneb, I., Fantinatob, C., and Collignon, A., New trends in *Clostridium difficile* virulence and pathogenesis, International Journal of Antimicrobial Agents, 2009 33:24-28.

Eastwood, K., Else P., Charlett, A., and Wilcox, M H., Comparison of Nine Commercially Available *Clostridium difficile* Toxin Detection Assays, a Real-Time PCR Assay for *C. difficile* tcdB, and a Glutamate Dehydrogenase Detection Assay to Cytotoxin Testing and Cytotoxigenic Culture Methods, J. Clin. Microbiol., October 2009, p. 3211-3217.

Hirvonen, J J., Mentula, S., Kaukoranta, S-S., Evaluation of a New Automated Homogeneous PCR Assay, GenomEra *C. difficile*, for Rapid Detection of Toxigenic *Clostridium difficile* in Fecal Specimens, J. Clin. Microbiol. 2013, 51 (9):2908. DOI: 10.1128/JCM.01083-13.

Houser, B A., Hattel, A L., and Jayarao, B M., Real-Time Multiplex Polymerase Chain Reaction Assay for Rapid Detection of *Clostridium difficile* Toxin-Encoding Strains, Foodborne Pathogens And Disease, 2010, 7 (6):719-726.

Knetsch, C W., Hensgens, M P M., Harmanus, C., van der Bijl, M W., Savelkoul, P H M., Kuijper, E J., Carver J., and van Leeuwen, H C., Genetic markers for *Clostridium difficile* lineages linked to hypervirulence, Microbiology (2011), 157, 3113-3123.

Rupnik, M., Wilcox, M H. and Gerding, D N, *Clostridium difficile* infection:

new developments in epidemiology and pathogenesis, Nature Reviews Microbiology 7, 526-536 (July 2009) p526, doi:10.1038/nrmicro2164.

The invention claimed is:

1. A method of detecting the presence of a hypervirulent *Clostridium difficile* strain in a biological sample, the method comprising:
performing a nucleic acid amplification reaction comprising DNA extracted from the biological sample as a template, a first oligonucleotide primer set specific for amplifying a target sequence in the *C. difficile* hydR gene in the reaction, wherein said hydR gene target sequence comprises at least part of the sequence set forth in SEQ ID NO: 1, and a second oligonucleotide primer set specific for amplifying at least part of the target sequence corresponding to *C. difficile* sequence set forth in SEQ ID NO:2 in the reaction.

2. The method according to claim 1, further comprising a step of detecting the presence of a hypervirulent *Clostridium difficile* strain in said biological sample, wherein the hypervirulent *Clostridium difficile* strain is detected in the sample, when the first oligonucleotide primer set does not amplify a specific product and the second oligonucleotide primer set amplifies a specific product.

3. The method according to claim 1, wherein the hypervirulent *Clostridium difficile* strain is *Clostridium difficile* strain 027 or a 027-ribotype-resembling *Clostridium difficile* strain.

4. The method according to claim 1, wherein the presence of *C. difficile* hydR gene DNA in said sample indicates that *Clostridium difficile* strain 027 is not present in the sample.

5. The method according to claim 1, wherein the *C. difficile*-specific target sequence for the first oligonucleotide primer set is a nucleotide region of an *C. difficile* hydR gene as set forth in SEQ ID NO: 1 and at least part of said nucleotide region is specifically amplified.

6. The method according to claim 5, wherein the first oligonucleotide primer set comprises an oligonucleotide comprising or consisting of at least 10 contiguous nucleotides present in the nucleotide sequence as set forth in SEQ ID NO: 3 and an oligonucleotide comprising or consisting of at least 10 contiguous nucleotides present in the nucleotide sequence as set forth in SEQ ID NO: 4.

7. The method according to claim 6, wherein the first oligonucleotide primer set comprises an oligonucleotide comprising or consisting of the nucleotide sequence as set forth in SEQ ID NO: 3 and an oligonucleotide comprising or consisting of the nucleotide sequence as set forth in SEQ ID NO: 4.

8. The method according to claim 1, wherein the presence of the target sequence amplified with the first oligonucleotide primer set is detected by the use of a probe comprising or consisting of at least 10 contiguous nucleotides present in the nucleotide sequence as set forth in SEQ ID NO:7.

9. The method according to claim 8, wherein the presence of the target sequence amplified with the first oligonucleotide primer set is detected by the use of a probe comprising or consisting of the nucleotide sequence as set forth in SEQ ID NO:7.

10. The method according to claim 1, wherein the second oligonucleotide primer set comprises an oligonucleotide comprising or consisting of at least 10 contiguous nucleotides present in a nucleotide sequence as set forth in SEQ ID NO: 5 and an oligonucleotide comprising or consisting of at least 10 contiguous nucleotides present in a nucleotide sequence as set forth in SEQ ID NO: 6.

11. The method according to claim 10, wherein the second oligonucleotide primer set comprises an oligonucleotide comprising or consisting of the nucleotide sequence as set forth in SEQ ID NO: 5 and an oligonucleotide comprising or consisting of the nucleotide sequence as set forth in SEQ ID NO: 6.

12. The method according to claim 1, wherein the presence of the target sequence amplified with the second oligonucleotide primer set is detected by the use of a probe comprising or consisting of the nucleotide sequence as set forth in SEQ ID NO:8 or 9.

13. The method according to claim 1, wherein the amplification reaction further comprises a third oligonucleotide primer set specific for amplifying *C. difficile* toxin B gene (tcdB) in the reaction and at least part of nucleotide region as set forth in SEQ ID NO: 10 is specifically amplified in the reaction.

14. The method according to claim 13, wherein the third oligonucleotide primer set comprises an oligonucleotide comprising or consisting of at least 10 contiguous nucleotides present in the nucleotide sequence as set forth in SEQ ID NO: 11 and an oligonucleotide comprising or consisting of at least 10 contiguous nucleotides present in the nucleotide sequence as set forth in SEQ ID NO: 12.

15. The method according to claim 14, wherein the third oligonucleotide primer set comprises an oligonucleotide comprising or consisting of the nucleotide sequence as set forth in SEQ ID NO: 11 and an oligonucleotide comprising or consisting of the nucleotide sequence as set forth in SEQ ID NO: 12.

16. The method according to claim 13, wherein the presence of the target sequence amplified with the third oligonucleotide primer set is detected by the use of a probe comprising or consisting of at least 10 contiguous nucleotides present in the nucleotide sequence as set forth in SEQ ID NO:13.

17. The method according to claim 16, wherein the presence of the target sequence amplified with the third oligonucleotide primer set is detected by the use of a probe comprising or consisting of the nucleotide sequence as set forth in SEQ ID NO: 13.

18. The method according to claim 1, wherein the biological sample is a stool sample or a food sample.

19. The method according to claim 2, wherein the detection of hypervirulent *Clostridium difficile* strain is performed using a DNA chip, gel electrophoresis, a radiation measurement, a fluorescence measurement, or a phosphorescence measurement.

20. The method according to claim 1, wherein the method is performed as a real-time PCR assay.

21. The method according to claim 1, wherein the nucleic acid amplification reaction is a PCR reaction.

22. The method according to claim 21, wherein the PCR reaction is performed as a real-time PCR assay.

23. The method according to claim 1, wherein the first oligonucleotide primer set amplifies at least 50 contiguous nucleotides of SEQ ID NO:1.

24. The method according to claim 1, wherein the second oligonucleotide primer set amplifies at least 50 contiguous nucleotides of SEQ ID NO:2.

25. The method according to claim 6, wherein the oligonucleotide comprising or consisting of at least 10 contiguous nucleotides present in the nucleotide sequence as set forth in SEQ ID NO: 3 and the oligonucleotide comprising or consisting of at least 10 contiguous nucleotides present in the nucleotide sequence as set forth in SEQ ID NO: 4 are each less than 30 nucleotides in length.

26. The method according to claim 6, wherein at least one oligonucleotide of the first oligonucleotide primer set comprises a modification selected from the group consisting of a base modification, a sugar modification, and a backbone modification.

27. The method according to claim 26, wherein at least one oligonucleotide of the first oligonucleotide primer set comprises a modified nucleotide selected from the group consisting of a LNA nucleotide, a minor groove binder (MGB)-conjugated nucleotide, a nucleotide with a Super-Base, and a PNA nucleotide.

28. The method according to claim 10, wherein the oligonucleotide comprising or consisting of at least 10 contiguous nucleotides present in a nucleotide sequence as set forth in SEQ ID NO: 5 and the oligonucleotide comprising or consisting of at least 10 contiguous nucleotides present in a nucleotide sequence as set forth in SEQ ID NO: 6 are each less than 30 nucleotides in length.

29. The method according to claim 10, wherein at least one oligonucleotide of the second oligonucleotide primer set comprises a modification selected from the group consisting of a base modification, a sugar modification, and a backbone modification.

30. The method according to claim 29, wherein at least one oligonucleotide of the first oligonucleotide primer set comprises a modified nucleotide selected from the group consisting of a LNA nucleotide, a minor groove binder (MGB)-conjugated nucleotide, a nucleotide with a Super-Base, and a PNA nucleotide.

\* \* \* \* \*

```
                       SEQUENCE LISTING

<160> NUMBER OF SEQ ID NOS: 13

<210> SEQ ID NO 1
<211> LENGTH: 232
<212> TYPE: DNA
<213> ORGANISM: Clostridium difficile 630

<400> SEQUENCE: 1
cgaacttcct ctattaaagc gaatgggatt ttttctaacc agctacaatg taccattttt      60
ctacgtgtgt aatcattcgc actatgaaca accaattcta ttattttttc atttgctgta     120
agggtgtcat cagcaacaag atactctaaa aaattattca tttgtgagta aagttctttt     180
gtgacacttc tcagtatatc ttctttagtt ttaaagtgat gatacattgc ac             232

<210> SEQ ID NO 2
<211> LENGTH: 119
<212> TYPE: DNA
<213> ORGANISM: Clostridium difficile 630

<400> SEQUENCE: 2
acggaaacat caaataacga attgacaatt tctgtagatt tcggtacgaa aacttcatgg      60
gaaagcagct tggtaaccca attaaatgaa ataccatata ataacattgg taaaggtac      119

<210> SEQ ID NO 3
<211> LENGTH: 20
<212> TYPE: DNA
<213> ORGANISM: Clostridium difficile 630

<400> SEQUENCE: 3
cgaacttcct ctattaaagc                                                  20

<210> SEQ ID NO 4
<211> LENGTH: 21
<212> TYPE: DNA
<213> ORGANISM: Clostridium difficile 630

<400> SEQUENCE: 4
gtgcaatgta tcatcacttt a                                                21

<210> SEQ ID NO 5
<211> LENGTH: 19
<212> TYPE: DNA
<213> ORGANISM: Clostridium difficile 630

<400> SEQUENCE: 5
```
acggaaacat caaataacg                                                  19

<210> SEQ ID NO 6
<211> LENGTH: 25
<212> TYPE: DNA
<213> ORGANISM: Clostridium difficile 630

<400> SEQUENCE: 6
gtacctttac caatgttatt atatg                                           25

<210> SEQ ID NO 7
<211> LENGTH: 27
<212> TYPE: DNA
<213> ORGANISM: Clostridium difficile 630

<400> SEQUENCE: 7
aatcattcgc actatgaaca accaatt                                         27

<210> SEQ ID NO 8
<211> LENGTH: 27
<212> TYPE: DNA
<213> ORGANISM: Clostridium difficile 630

<400> SEQUENCE: 8
tctgtagatt tcggtacgaa aacttca                                         27

<210> SEQ ID NO 9
<211> LENGTH: 27
<212> TYPE: DNA
<213> ORGANISM: Clostridium difficile 630

<400> SEQUENCE: 9
tctgtagatt ttggtacgaa aacttca                                         27

<210> SEQ ID NO 10
<211> LENGTH: 171
<212> TYPE: DNA
<213> ORGANISM: Clostridium difficile 630

<400> SEQUENCE: 10
ggaagtgaat gtatatgaaa acctaagtag atattagtat attttataaa tagaaaggag     60
gatatataaa agagttttag catttagatg taaaaatatt caataaaaat attatagtaa    120
aggagaaaat tttatgagtt tagttaatag aaaacagtta gaaaaaatgg c             171

<210> SEQ ID NO 11
<211> LENGTH: 23
<212> TYPE: DNA
<213> ORGANISM: Clostridium difficile 630

<400> SEQUENCE: 11
ggaagtgaat gtatatgaaa acc                                             23

<210> SEQ ID NO 12
<211> LENGTH: 22
<212> TYPE: DNA
<213> ORGANISM: Clostridium difficile 630

<400> SEQUENCE: 12 gccattttttt ctaactgttt tc                                             22

<210> SEQ ID NO 13
<211> LENGTH: 30

```
<212> TYPE: DNA
<213> ORGANISM: Clostridium difficile 630

<400> SEQUENCE: 13
agaaaggagg atatataaaa gagttttagc                                            30
```

UNITED STATES PATENT AND TRADEMARK OFFICE
CERTIFICATE OF CORRECTION

PATENT NO. : 11,566,294 B2
APPLICATION NO. : 15/532132
DATED : January 31, 2023
INVENTOR(S) : Juha Kirveskari et al.

It is certified that error appears in the above-identified patent and that said Letters Patent is hereby corrected as shown below:

On the Title Page

1. In Item (56), under "OTHER PUBLICATIONS", in Column 2, Line 1, delete "107(16) 7527-7532)" and insert -- 107(16):7527-7532) --, therefor.
2. In Item (56), under "OTHER PUBLICATIONS", in Column 2, Line 4, delete "p." and insert -- pp. --, therefor.
3. In Item (56), under "OTHER PUBLICATIONS", in Column 2, Line 6, delete "p." and insert -- pp. --, therefor.
4. In Item (56), under "OTHER PUBLICATIONS", in Column 2, Line 23, delete "ilvd" and insert -- Ilvd --, therefor.
5. In Item (56), under "OTHER PUBLICATIONS", in Column 2, Line 39, delete "Micorbiology," and insert -- Microbiology, --, therefor.
6. On Page 2, In Item (56), under "OTHER PUBLICATIONS", in Column 1, Line 20, delete "p." and insert -- pp. --, therefor.
7. On Page 2, In Item (56), under "OTHER PUBLICATIONS". in Column 1, Line 22, delete "Crostridium" and insert -- Clostridium --, therefor.

In the Specification

8. In Column 1, Line 5, delete "Held" and insert -- field --, therefor.
9. In Column 1, Line 15, delete "OP" and insert -- OF --, therefor.
10. In Column 1, Line 28, delete "et al." and insert -- et al., --, therefor.
11. In Column 1, Line 34, delete "et al." and insert -- et al., --, therefor.
12. In Column 1, Line 38, delete "2009," and insert -- 2009; --, therefor.
13. In Column 3, Line 2, delete "associated ribotype" and insert -- associated with ribotype --, therefor.
14. In Column 4, Line 15, delete "1, 3, 4" and insert -- 1, 2, 3, 4 --, therefor.
15. In Column 6, Line 61, delete "with probe" and insert -- with a probe --, therefor.
16. In Column 7, Line 64, delete "non-toxinogenic" and insert -- non-toxigenic --, therefor.

Signed and Sealed this
Seventeenth Day of October, 2023

Katherine Kelly Vidal
*Director of the United States Patent and Trademark Office*

CERTIFICATE OF CORRECTION (continued)
U.S. Pat. No. 11,566,294 B2

17. In Column 8, Line 1, delete "commercial" and insert -- commercially --, therefor.
18. In Column 8, Line 26, delete "AKC 43602" and insert -- ATCC 43602 --, therefor.
19. In Column 8, Line 52, delete "gPCR" and insert -- qPCR --, therefor.
20. In Columns 9-10, Table 3, Line 33, delete "RHC7722" and insert -- RHC 7722 --, therefor.
21. In Column 10, Line 7, delete "hydR+)." and insert -- hydR-). --, therefor.
22. In Column 11, Line 3, delete "DATA" and insert -- DNA --, therefor.
23. In Column 12, Line 8, delete "to the" and insert -- in the --, therefor.
24. In Column 12, Lines 37-38, delete "identification identification" and insert -- identification --, therefor.
25. In Column 13, Line 61, delete "gPCR" and insert -- qPCR --, therefor.
26. In Column 13, Line 66, delete "that that" and insert -- that --, therefor.
27. In Column 15, Line 4, delete "PCR" and insert -- qPCR --, therefor.
28. In Column 15, Line 9, delete "included to" and insert -- included in --, therefor.
29. In Column 15, Line 10, delete "including to the" and insert -- including the --, therefor.
30. In Column 16, Line 18, delete "commercial" and insert -- commercially --, therefor.
31. In Column 16, Line 19, delete "Microbiologics Qnostics" and insert -- Microbiologies, Qnostics --, therefor.
32. In Columns 15 and 16, Table 7, Entry No. 23, delete "Citrobacter koserii" and insert -- Citrobacter koseri --, therefor.
33. In Columns 15 and 16, Table 7, Entry No. 33, delete "Cryptosporidiumn parvum" and insert -- Cryptosporidium parvum --, therefor.
34. In Columns 15 and 16, Table 7, Entry No. 96, delete "Providencia rettqeri" and insert -- Providencia rettgeri --, therefor.
35. In Columns 15 and 16, Table 7, Entry No. 99, delete "Raoutella ornithinolytica" and insert -- Raoultella ornithinolytica --, therefor.
36. In Columns 15 and 16, Table 7, Entry No. 102, delete "Saccharomyces kudriaczevii" and insert -- Saccharomyces kudriavzevii --, therefor.
37. In Columns 17 and 18, Table 7, Entry No. 55, delete "Escherichia hermanii" and insert -- Escherichia hermannii --, therefor.
8. In Columns 17 and 18, Table 7, Entry No. 124, delete "Vibrio parhaemolyticus" and insert -- Vibrio parahaemolyticus --, therefor.
39. In Column 18, Table 10, Line 57, delete "CATTG" and insert -- CATTTG --, therefor.
40. In Column 20, Line 6, delete "7 (6):719-726." and insert -- 7(6):719-726. --, therefor.
41. In Column 20, Line 8, delete "Carver J.," and insert -- Corver J., --, therefor.
42. In Column 20, Line 14, delete "new" and insert -- New --, therefor.

In the Claims

43. In Column 23, Line 42, in Claim 5, delete "an C." and insert -- a C. --, therefor.